(12) United States Patent
Wheatley

(10) Patent No.: US 11,911,267 B2
(45) Date of Patent: Feb. 27, 2024

(54) HEART VALVE

(71) Applicant: The David J. Wheatley Discretionary Trust, Glasgow (GB)

(72) Inventor: David J. Wheatley, Glasgow (GB)

(73) Assignee: The David J. Wheatley Discretionary Trust, Glasgow (GB)

( * ) Notice: Subject to any disclaimer, the term of this patent is extended or adjusted under 35 U.S.C. 154(b) by 748 days.

(21) Appl. No.: 17/051,721

(22) PCT Filed: Apr. 25, 2019

(86) PCT No.: PCT/GB2019/051154
§ 371 (c)(1),
(2) Date: Oct. 29, 2020

(87) PCT Pub. No.: WO2019/211581
PCT Pub. Date: Nov. 7, 2019

(65) Prior Publication Data
US 2021/0186688 A1 Jun. 24, 2021

(30) Foreign Application Priority Data
May 1, 2018 (GB) ...................................... 1807169

(51) Int. Cl.
*A61F 2/24* (2006.01)
(52) U.S. Cl.
CPC ............ *A61F 2/2418* (2013.01); *A61F 2/243* (2013.01); *A61F 2/2439* (2013.01); *A61F 2220/0025* (2013.01)
(58) Field of Classification Search
CPC ...... A61F 2/2418; A61F 2/243; A61F 2/2439; A61F 2220/0025; A61F 2250/006; A61F 2/2412; A61F 2/24; A61M 29/00
See application file for complete search history.

(56) References Cited

U.S. PATENT DOCUMENTS

| | | | |
|---|---|---|---|
| 2005/0075731 A1* | 4/2005 | Artof ................... | A61F 2/2439 623/2.18 |
| 2005/0137686 A1* | 6/2005 | Salahieh ............... | A61F 2/2439 623/2.11 |

(Continued)

FOREIGN PATENT DOCUMENTS

| | | |
|---|---|---|
| WO | 2007009117 A1 | 1/2007 |
| WO | 2008068756 A2 | 6/2008 |
| WO | 2016097337 A1 | 1/2016 |

OTHER PUBLICATIONS

Search report dated Oct. 22, 2018 in counterpart application No. GB44172GB. 3 pages.

(Continued)

*Primary Examiner* — Kelly J Bekker
*Assistant Examiner* — Andrew P. Restaino
(74) *Attorney, Agent, or Firm* — Blank Rome LLP

(57) ABSTRACT

An artificial heart valve suitable to be delivered percutaneously, comprises a plurality of support elements in the form of a plurality of base segments and a plurality of posts; a plurality of flexible leaflets, each leaflet attached to two of the posts; and one or more strings passing through the plurality of support elements. The artificial heart valve is configurable between a collapsed delivery configuration in which the posts are located side-by-side and closer together and an expanded operational configuration in which the posts are located side-by-side and further apart. When the artificial heart valve is in the collapsed delivery configuration, application of tension to the one or more strings pulls each support element into engagement with adjacent support elements until the artificial heart valve adopts the expanded operational configuration in which the support elements together form a support structure defining an aperture for blood flow.

19 Claims, 14 Drawing Sheets

(56) References Cited

U.S. PATENT DOCUMENTS

| | | |
|---|---|---|
| 2008/0221672 A1 | 9/2008 | Endovalve |
| 2011/0172764 A1 | 7/2011 | Badhwar |
| 2015/0157455 A1 | 6/2015 | Hoang et al. |
| 2016/0270911 A1* | 9/2016 | Ganesan .............. A61F 2/2436 |

OTHER PUBLICATIONS

International Search report dated Jul. 7, 2019 in counterpart application No. PCT/GB2019/051154. 8 pages.

* cited by examiner

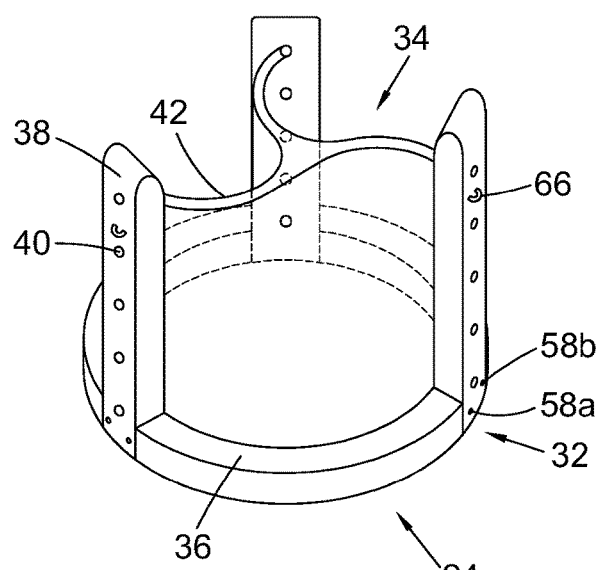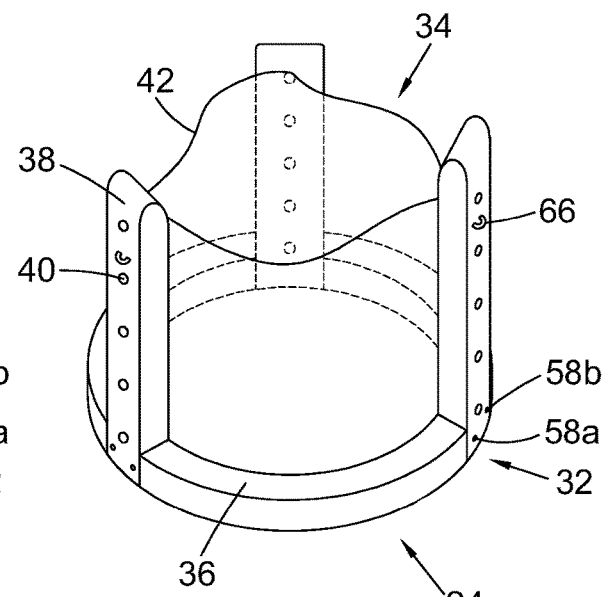
Fig. 4A  Fig. 4B
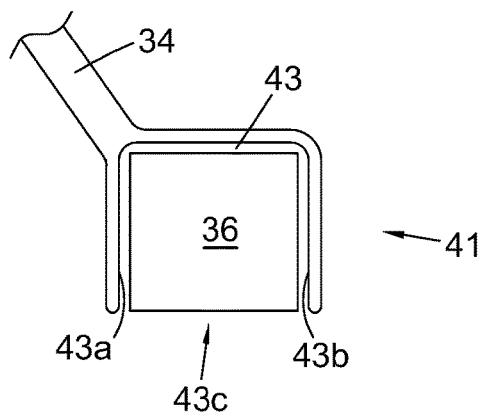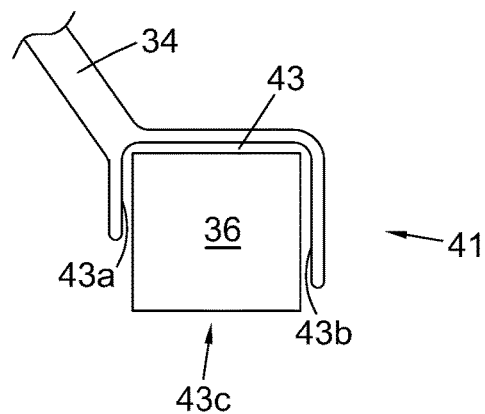
Fig. 5A  Fig. 5B

HEART VALVE

FIELD

The present disclosure relates to an artificial heart valve, a stent and an artificial heart valve system suitable for percutaneous delivery and methods for the percutaneous delivery of such an artificial heart valve, a stent and an artificial heart valve system.

BACKGROUND

The valves of the heart may be abnormal from birth, may become diseased, or may degenerate in old age. When their function becomes sufficiently impaired they may require to be replaced. There are many different types of artificial heart valves in established clinical use for the replacement of abnormal or aged natural heart valves. Mechanical replacement heart valves are typically constructed of rigid materials such as metallic alloys, pyrolytic carbon, or rigid polymers. They do not generally resemble natural heart valves. Biological replacement heart valves generally have leaflets constructed of flexible materials of human or animal origin such as human aortic or pulmonary valves, animal aortic or venous valves, or animal pericardium (the fibrous sheet surrounding the heart). Such animal tissues are commonly treated with agents such as glutaraldehyde to enhance their durability. Biological heart valves generally resemble the natural aortic or pulmonary valves. Artificial heart valves are also known, having flexible synthetic materials fashioned into flexible leaflets on a supporting frame. Some of these artificial heart valves have synthetic leaflets which differ appreciably in configuration from the leaflets of natural heart valves.

Valves have traditionally been implanted into the heart after removal of the abnormal valve by means of open-heart surgery. More recently, flexible valve leaflets have been attached within an expandable mesh-like cylinder or stent, for percutaneous delivery on a catheter. An antegrade approach may be used wherein the catheter is introduced into the apex of the heart. Or, a retrograde approach may be used wherein the catheter is introduced via a peripheral blood vessel. After manipulation into the correct location, the stent and artificial heart valve are expanded with a balloon to create a functional valve. Such known methods of percutaneously implanting a heart valve, although less invasive than an open-heart operation, have some drawbacks. The pressure applied to the flexible leaflets between the balloon and the stent during expansion can cause damage, such as tearing, to the flexible leaflets. If the flexible leaflets are damaged they may not function effectively.

During open-heart surgery, a peripheral portion of the heart valve is sewn into a region of natural valve leaflet attachment known as the valve annulus. The peripheral portion of the heart valve may be formed of a resilient material so that a seal is provided between the artificial heart valve and the artery wall when the peripheral portion of the heart valve is sewn into the valve annulus. This prevents a loss of efficiency in the functioning of the valve. Sewing the valve into the valve annulus is not possible percutaneously.

SUMMARY

An artificial heart valve is described herein which is suitable to be delivered percutaneously. The artificial heart valve comprises a plurality of support elements in the form of a plurality of base segments and a plurality of posts. The artificial heart valve further comprises a plurality of flexible leaflets. Each leaflet is attached to two of the posts. The artificial heart valve further comprises one or more strings passing through the plurality of support elements. The artificial heart valve is configurable between a collapsed delivery configuration in which the posts are located side-by-side and closer together and an expanded operational configuration in which the posts are located side-by-side and further apart. When the artificial heart valve is in the collapsed delivery configuration, application of tension to the one or more strings pulls each support element into engagement with adjacent support elements until the artificial heart valve adopts the expanded operational configuration in which the support elements together form a support structure defining an aperture for blood flow in which the leaflets are movable between an open configuration in which the leaflets permit blood flow through the artificial heart valve and a closed configuration in which the leaflets restrict blood flow through the artificial heart valve.

Such an artificial heart valve may be delivered percutaneously. Such an artificial heart valve does not require the leaflets to be compressed between a balloon and a stent during expansion. Consequently, such an artificial heart valve may be less prone to damage during expansion than known artificial heart valves which are delivered percutaneously and expanded using a balloon.

When the artificial heart valve is in the expanded operational configuration, the support elements may be in compression. When the artificial heart valve is in the collapsed delivery configuration the support elements may not be in compression.

The support structure may be generally annular or generally cylindrical. The support structure may be generally shaped to correspond to the shape of the aorta.

The number and/or distribution of base segments located between adjacent posts may be selected according to the size and/or shape of the valve annulus. The number of and/or distribution of base segments located between adjacent posts may be selected according to the size and/or shape of the leaflets attached to the adjacent posts.

The posts may be distributed circumferentially around the support structure with an equal number of base segments located between adjacent posts.

The posts may be distributed circumferentially around the support structure with an unequal number of base segments located between adjacent posts. For example, for a bicuspid valve such as a mitral valve having only first and second leaflets attached between first and second posts, the number of base segments extending along the base edge of the first leaflet may be different to the number of base segments extending along the base edge of the second leaflet, for example to accommodate different sizes and/or shapes of the first and second leaflets.

The artificial heart valve may comprise a plurality of base segments between each pair of adjacent posts. The artificial heart valve may comprise 10 to 16 base segments between each pair of adjacent posts.

Adjacent support elements may define complementary surfaces which are in engagement when the artificial heart valve is in the expanded operational configuration.

Each post may have a base portion. For each post, the base portion of the post and the base segment adjacent to the base portion of the post may define complementary surfaces which are in engagement when the artificial heart valve is in the expanded operational configuration.

When the artificial heart valve is in the expanded operational configuration, each leaflet may extend over one or more of the base segments between the two posts to which the leaflet is attached.

Each leaflet may define a base edge. The base edge may define a channel or recess. The channel or recess may have an internal profile. The one or more base segments between the two posts to which the leaflet is attached may define an external profile. The internal profile of the channel or recess may be complementary to the external profile defined by the one or more base segments between the two posts to which the leaflet is attached.

When the artificial heart valve is in the expanded operational configuration, the flexible leaflets may provide a seal between the support structure and the stent. When the artificial heart valve is in the expanded operational configuration, the flexible leaflets may provide a smooth surface for flow of blood through the aperture for blood flow.

Each of the flexible leaflets may comprise a polymer. The polymer may be polyurethane such as biostable polyurethane. Such polymer flexible leaflets may be resilient to folding. Furthermore, biostable polyurethane does not generally calcify in use, therefore the length of time for which the artificial heart valve can be used in the human body may be extended.

The support elements may be formed using an additive manufacturing technique such as direct laser sintering or 3D printing to provide an accurate and/or complex shape. Sintering and/or 3D printing may provide the support elements with a rough surface which can improve adhesion of the flexible leaflets to the support elements. The support elements may comprise a metal. The support elements may comprise titanium. The support elements may be formed using direct laser metal sintering.

Each flexible leaflet may be bonded or fused to at least one base segment located between the posts to which the flexible leaflet is attached. This may cause the base segments to preferentially locate in the channel or recess defined by the base edge of the flexible leaflet when the artificial heart valve is in the collapsed delivery configuration and tension is applied to the one or more strings. Furthermore, when the artificial heart valve is in the collapsed delivery configuration, this may result in a reduction in an axial distance over which the base segments extend, wherein the axial distance is defined relative to an axis defined by the aperture for blood flow. In effect, this may reduce the overall axial extent of the artificial heart valve in the collapsed delivery configuration. During delivery of the artificial heart valve through an artery, the heart may spontaneously eject blood through the artery and cause damage to the leaflets as the base segments are caught in the blood flow. Reducing the axial distance over which the base segments extend, may reduce the chance of damage to the leaflets because the base segments have less freedom of movement when disturbed by the blood flow.

When the artificial heart valve is in the expanded operational configuration, each leaflet may have a moveable free edge and a base edge opposite the free edge.

When the artificial heart valve is in the expanded operational configuration, the base segments between each pair of adjacent posts may be arranged along an outwardly convex path in a transverse plane relative to an axis defined by the aperture for blood flow. When the artificial heart valve is in the expanded operational configuration, the moveable free edge of each leaflet may be generally S-shaped and the base edge of each leaflet may be outwardly convex relative to the axis defined by the aperture for blood flow. Such a leaflet may fold in a predictable manner between the posts to which the leaflet is attached (rather than crumpling unpredictably) when the artificial heart valve is folded or manipulated into the collapsed delivery configuration and mounted on a catheter for percutaneous delivery. Such leaflets may, therefore, be particularly suitable for percutaneous delivery, as such leaflets may be subject to relatively low levels of stress when the artificial heart valve is folded or manipulated into the collapsed delivery configuration and mounted on a catheter for percutaneous delivery.

When the artificial heart valve is in the expanded operational configuration, the base edge of each leaflet may be arranged along an outwardly convex path having both circumferential and axial components relative to an axis defined by the aperture for blood flow. For example, the base edge of each leaflet may be "scallop shaped".

When the artificial heart valve is in the expanded operational configuration, the moveable free edge of each leaflet may be generally outwardly convex when the leaflet is in the open configuration and the moveable free edge of each leaflet may be generally outwardly concave when the leaflet is in the closed configuration.

When the artificial heart valve is in the expanded operational configuration, the base segments between each pair of adjacent posts may be arranged along an outwardly convex path having both circumferential and axial components relative to an axis defined by the aperture for blood flow.

The artificial heart valve may comprise a sleeve. The sleeve may be located radially outwardly of the flexible leaflets. The sleeve may provide protection for the flexible leaflets during percutaneous delivery of the artificial heart valve.

An artificial heart valve system is described herein which is suitable to be delivered percutaneously. The artificial heart valve system comprises the previously described artificial heart valve, and a stent configurable between a collapsed delivery configuration and an expanded operational configuration. The one or more strings pass through the stent. When the stent is in its expanded operational configuration and the artificial heart valve is in its collapsed delivery configuration, application of tension to the one or more strings pulls each support element into engagement with the adjacent support elements and pulls the posts into engagement with the stent until the artificial heart valve adopts the expanded operational configuration and is in engagement with the stent.

Such an artificial heart valve system may be delivered percutaneously. Such an artificial heart valve system does not require the leaflets to be compressed between a balloon and a stent during expansion. Consequently, such an artificial heart valve system is likely to be less prone to damage during expansion than known artificial heart valve systems which are delivered percutaneously and expanded using a balloon.

Such an artificial heart valve system may provide a good seal with an artery wall.

One or more strings may pass alternatingly through the stent and the plurality of support elements of the artificial heart valve.

The artificial heart valve may be pulled into axial alignment with the stent when tension is applied to the one or more strings.

The stent may comprise at least one string guidance feature corresponding to each post. The one or more strings may extend through the at least one string guidance feature. When the stent is in its expanded operational configuration and the artificial heart valve is in its expanded operational configuration, each post may abut the stent at a location adjacent the corresponding at least one string guidance feature.

Each post may comprise a plurality of tunnels through which the one or more strings pass. Each base segment may comprise a tunnel through which the one or more strings pass.

For each post, the one or more strings may pass from at least one of the tunnels of the post through a corresponding string guidance feature of the stent.

Each post may comprise a string guidance feature.

For each post, the one or more strings may pass from at least one of the tunnels of the post through a first corresponding string guidance feature of the stent, through the corresponding string guidance feature of the post and through a second corresponding string guidance feature of the stent.

The one or more strings may comprise a single continuous string. On application of tension to the single continuous string, said tension is distributed more evenly to the plurality of support elements.

The one or more strings may comprise a plurality of strings. For each pair of adjacent posts, one of the strings may extend through each base segment located between the pair of adjacent posts, through the pair of adjacent posts, and through the stent.

The one or more strings comprise a plurality of strings, and, for each pair of adjacent posts, two or more of the strings extend through each base segment located between the pair of adjacent posts, through the pair of adjacent posts, and through the stent.

The one or more strings may comprise a plurality of strings, and, for each pair of adjacent posts, two or more of the strings may extend through each base segment located between the pair of adjacent posts, through the pair of adjacent posts, and through the stent The artificial heart valve system may comprise a plurality of anchor strings. For each post, a corresponding anchor string may extend through a string guidance feature of the post and through a string guidance feature of the stent without extending through any of the base segments When the stent is in its expanded operational configuration and the artificial heart valve is in its expanded operational configuration, the support structure may abut a surface of the stent which is radially inward relative to an axis defined by the aperture for blood flow.

The artificial heart valve system may comprise a plurality of string locking arrangements. Each string locking arrangement may be configured to allow the one or more strings to be pulled in a first direction relative to the stent but to prevent the one or more strings from being pulled relative to the stent in a second direction opposite to the first direction. Each string locking arrangement may comprise a male locking element attached to the one or more strings and a female locking element attached to the stent, wherein the male and female locking elements may be configured to allow the male locking element to be pulled with the one or more strings in a first direction through the female locking element but to prevent the male locking element from being pulled through the female locking element with the one or more strings in a second direction opposite to the first direction. The male and female locking elements may define complementary inter-engaging ratchet profiles.

The artificial heart valve system may further comprise a sealing arrangement configured to provide a seal between the artificial heart valve and the stent when the stent is in its expanded operational configuration and the artificial heart valve is in its expanded operational configuration. The sealing arrangement may extend around a base portion of the stent. The sealing arrangement may comprise a sealing member and a flexible sealing actuation string extending around a periphery of the sealing member. When the stent is in its expanded operational configuration and the artificial heart valve is in its expanded operational configuration, tension applied to the sealing actuation string may compress the sealing member and the plurality of flexible leaflets against the support structure. The sealing member may comprise a woven material such as woven polyester cloth. Sealing between the artificial heart valve and the stent may improve the efficiency of the artificial heart valve because flow of blood may pass through the aperture of the artificial heart valve, rather than between the artificial heart valve and the stent.

The support elements may be rigid.

A plurality of support elements for an artificial heart valve is described herein. The plurality of support elements comprises a plurality of base segments and a plurality of posts. The plurality of support elements is configurable between a collapsed delivery configuration in which the posts are located side-by-side and closer together and an expanded operational configuration in which the posts are located side-by-side and further apart. The plurality of support elements is configured such that, when the plurality of support elements is in the collapsed delivery configuration, application of tension to one or more strings passing through the plurality of support elements, pulls each support element into engagement with adjacent support elements until the plurality of support elements adopts the expanded operational configuration in which the support elements together form a support structure defining an aperture for blood flow.

A method of percutaneously implanting the artificial heart valve system into a human or animal subject is described herein.

The method may comprise mounting the artificial heart valve system on a catheter. The method may comprise mounting the artificial heart valve system on a catheter with the stent and the artificial heart valve in their respective collapsed delivery configurations.

The method may comprise mounting the stent and an inflatable member on the catheter at a first axial location of the catheter with the stent located radially outwardly of the inflatable member. The method may comprise mounting the artificial heart valve on the catheter at a second axial location of the catheter.

The second axial location of the artificial heart valve on the catheter may be proximal with respect to the first axial location of the stent and the inflatable member.

The second axial location of the artificial heart valve on the catheter may be distal with respect to the first axial location of the stent and the inflatable member.

The method may comprise inserting the catheter through an incision in the skin of the subject. The method may comprise inserting the catheter through an artery of the subject. The method may comprise aligning the stent and the inflatable member adjacent a valve annulus of the subject.

The method may comprise inflating the inflatable member to expand the stent from its collapsed delivery configuration to its expanded operational configuration. The method may comprise deflating the inflatable member after expansion of the stent. The method may then comprise moving the catheter relative to the subject until the artificial heart valve is generally aligned axially with the stent.

For example, if the second axial location of the artificial heart valve on the catheter is proximal with respect to the first axial location of the stent and the inflatable member, the method may comprise initially inserting the catheter into the subject until the stent and the inflatable member are generally aligned axially with the valve annulus and the artificial heart valve is located proximal of the valve annulus. The method may then comprise inflating the inflatable member to expand the stent from its collapsed delivery configuration to its expanded operational configuration. The method may comprise deflating the inflatable member after expansion of the stent. The method may comprise inserting the catheter further into the subject until the artificial heart valve is generally aligned axially with the stent and the inflatable member is inserted distally of the stent. Mounting the artificial heart valve on the catheter at a second axial location which is proximal with respect to the first axial location of the stent and the inflatable member, may avoid any requirement for the artificial heart valve to be inserted into, or through, the valve annulus before expansion of the stent.

Alternatively, if the second axial location of the artificial heart valve on the catheter is distal with respect to the first axial location of the stent and the inflatable member, the method may comprise inserting the catheter into the subject so as to insert the artificial heart valve through the valve annulus until the stent and the inflatable member are generally aligned axially with the valve annulus. The method may comprise inflating the inflatable member to expand the stent from its collapsed delivery configuration to its expanded operational configuration. The method may comprise deflating the inflatable member after expansion of the stent. The method may comprise retracting the catheter from the subject until the artificial heart valve is generally aligned axially with the stent and the inflatable member is proximal of the stent.

The method may comprise removing the sleeve.

The method may comprise applying tension to the one or more strings so as to expand the artificial heart valve from the collapsed delivery configuration to the expanded operational configuration and so as to pull the artificial heart valve radially outwardly into engagement with the stent.

The method may comprise applying the tension to the one or more the strings using one or more secondary strings, wherein each secondary string extends from the incision in the skin of the subject, through a corresponding loop in the one or more strings, and returns to the incision in the skin.

The method may comprise withdrawing the catheter and the deflated inflatable member from the subject.

BRIEF DESCRIPTION OF THE DRAWINGS

Artificial heart valves, stents, artificial heart valve systems and methods will now be described by way of non-limiting example only with reference to the following drawings of which:

FIG. 4A is a perspective view of an artificial heart valve of the artificial heart valve system of FIG. 1 in a closed configuration;

FIG. 4B is a perspective view of an artificial heart valve of the artificial heart valve system of FIG. 1 in an open configuration;

FIG. 5A is a schematic cross section of a base portion of the artificial heart valve of FIGS. 4A and 4B when the artificial heart valve is in an expanded operational configuration;

FIG. 5B is a schematic cross section of an alternative base portion of the artificial heart valve of FIGS. 4A and 4B when the artificial heart valve is in an expanded operational configuration;

DETAILED DESCRIPTION OF DRAWINGS

Figure 1:
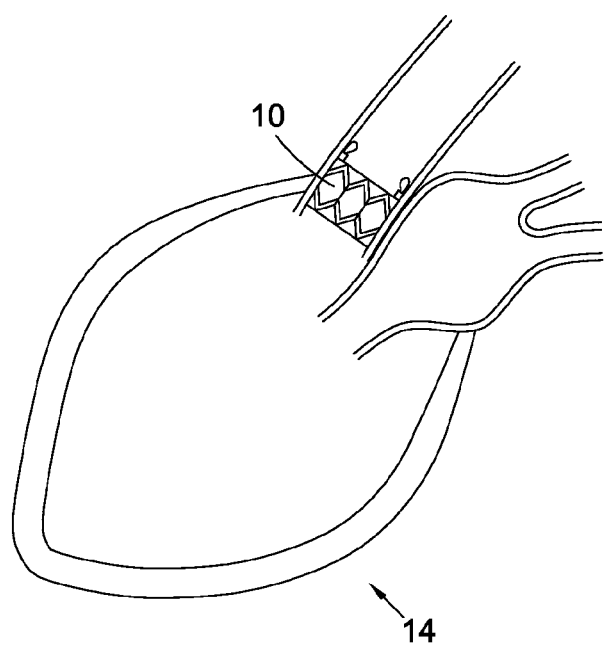
FIG. 1 is a schematic cut-away perspective view of a heart following percutaneous delivery of an artificial heart valve system to replace the natural aortic valve.

Referring initially to FIG. 1, there is shown a heart 14 following percutaneous delivery of an artificial heart valve system 10 to replace, or displace, the natural, abnormal, aortic valve.

Figure 2:
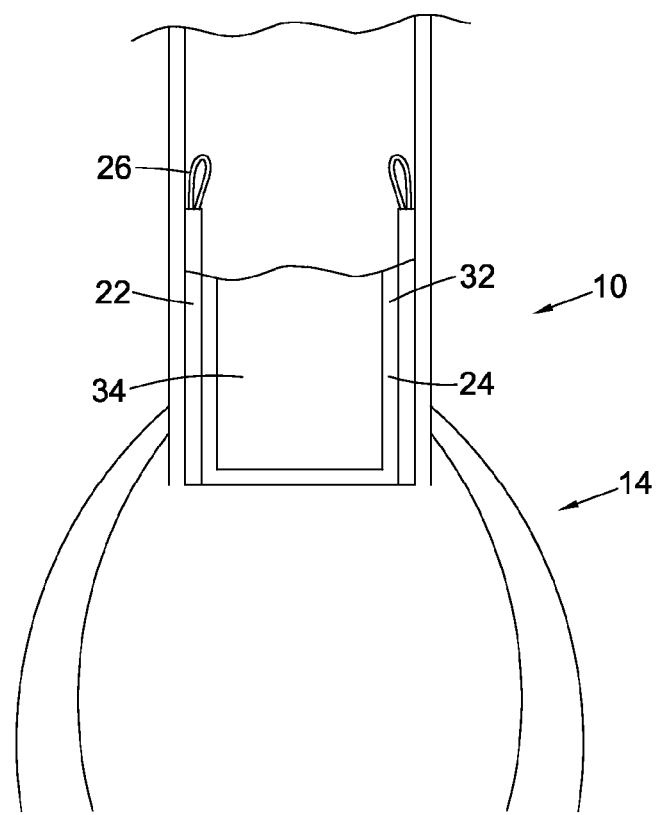
FIG. 2 is a detailed schematic section of the artificial heart valve system of FIG. 1.
Figure 3:
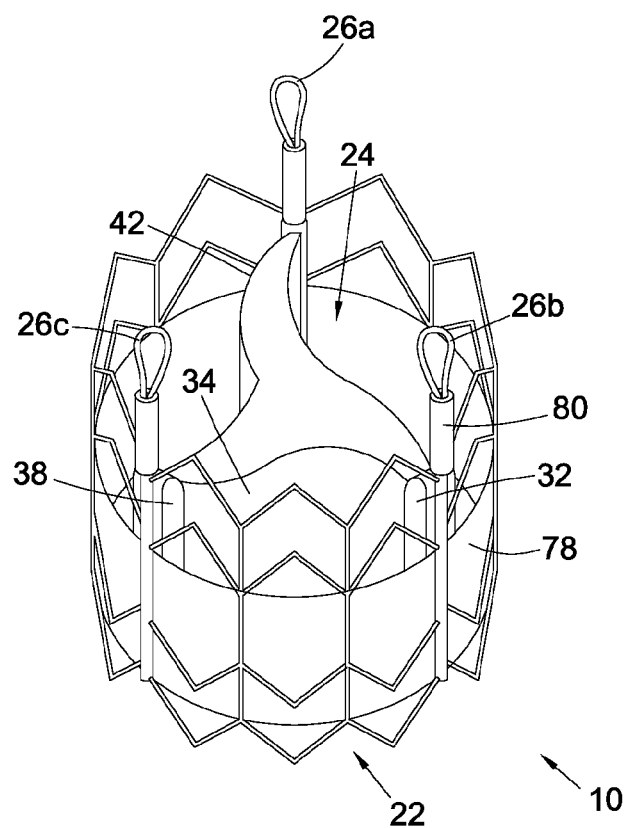
FIG. 3 is a perspective view of the artificial heart valve system of FIG. 1.

Referring to FIGS. 2 and 3 the artificial heart valve system 10 has a stent 22 and an artificial heart valve 24. As will be described in more detail below, the artificial heart valve 24 has a plurality of support elements and a plurality of flexible leaflets 34 attached to the support elements. The support elements are rigid. The artificial heart valve 24 has a collapsed delivery configuration and an expanded operational configuration, as will be described in more detail below. The stent 22 also has a collapsed delivery configuration and an expanded operational configuration.

FIGS. 4A and 4B show an artificial heart valve 24 in its expanded operational configuration when the flexible leaflets 34 are in closed and open positions respectively. The artificial heart valve 24 has three flexible leaflets 34. When the artificial heart valve 24 in its expanded operational configuration, the support elements together form a support structure 32. The support structure 32 has a base 36, and three rigid posts 38. When the artificial heart valve 24 is in the expanded operational configuration, the base 36 is generally annular. Each post 38 has a series of holes 40. A continuous layer of polymer is formed around each post 38 and through the holes 40 in each post 38. The polymer between two adjacent posts 38 forms one of the flexible leaflets 34.

Each flexible leaflet 34 has an upper edge 42. When the artificial heart valve 24 in its expanded operational configuration, the upper edge 42 is a moveable free edge. The free edge 42 of each flexible leaflet 34 has an approximate "S" shape. The flexible leaflets 34 are translucent. Consequently, the flexible leaflets 34 are indicated in FIGS. 4A and 4B by a solid line showing the free edge 42 of each flexible leaflet 34. When the artificial heart valve is in the expanded operational configuration, the free edge 42 is movable between a closed position in which blood flow through the artificial heart valve is restricted (see FIG. 4A), and an open position in which blood flow through the artificial heart valve is permitted (see FIG. 4B). In the closed position, the upper portions or co-aptation regions of the flexible leaflets 34 engage one another so as to form a seal. In the open position, the co-aptation regions of the flexible leaflets 34 are spaced apart.

Each flexible leaflet 34 has a base edge or portion 41 opposite the free edge 42. The base edge 41 is outwardly convex relative to an axis defined by the support structure. The base edge or portion 41 of each flexible leaflet 34 defines a channel or recess 43 defining an internal profile which is complementary to an external profile of the base 36. Each channel 43 has a radially inner surface 43a, a radially outer surface 43b and an opening for receiving a portion of the base 36 when the artificial heart valve 24 is in the expanded operational configuration. The radially inner surface 43a can extend the full depth of the base 36 (see FIG. 5A), or only a partial depth of the base 36 (see FIG. 5B). When the artificial heart valve is in the expanded operational configuration, the internal profile of the channel or recess 43 extends over the base 36 between the two posts to which the leaflet is attached.

Figure 6A:
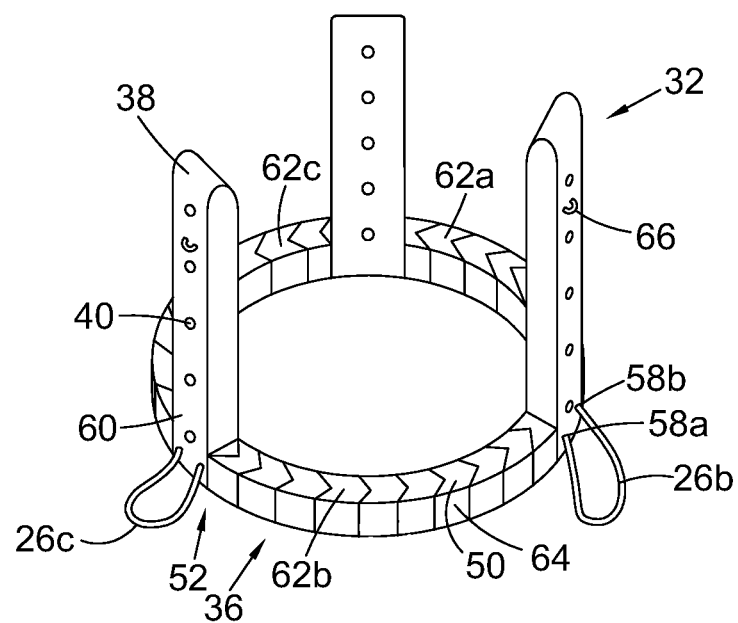
FIG. 6A is a perspective view of a plurality of support elements of the artificial heart valve of FIGS. 4A and 4B when the artificial heart valve is in an expanded operational configuration and each support element is pulled into engagement with the adjacent support elements so as to define a support structure in which the support elements are in compression.
Figure 6B:
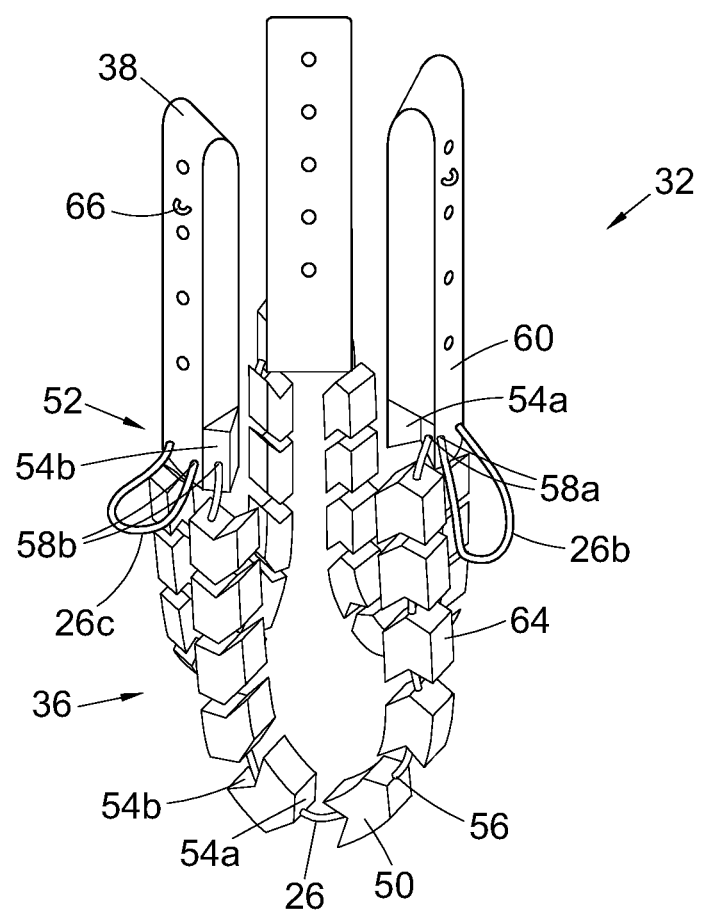
FIG. 6B is a perspective view of a plurality of support elements of the artificial heart valve of FIGS. 4A and 4B when the artificial heart valve is in a collapsed delivery configuration and the support elements are not in compression.

As shown in FIGS. 6A and 6B, the base 36 is formed from a plurality of base segments 50. Each base segment 50 constitutes a support element of the artificial heart valve 24. Similarly, each post 38 constitutes a support element the artificial heart valve 24. As will be described in more detail below, FIG. 6A shows the plurality of support elements when the artificial heart valve is in an expanded operational configuration and each support element is pulled into engagement with the adjacent support elements so as to define the support structure 32 in which the support elements are in compression and FIG. 6B shows the plurality of support elements when the artificial heart valve is in a collapsed delivery configuration and the support elements are not in compression.

Each post 38 has a base portion 52. The base portion 52 of post 38 is the portion of post 38 adjacent the base segments 50 of the support structure 32. The base segments are grouped into three groups 62a, 62b, 62c, with each group 62a, 62b, 62c of base segments 50 located between two adjacent posts 38. In FIGS. 6A and 6B there are ten base segments 50 per group 62. When the artificial heart valve 24 is in the expanded operational configuration, each group 62 of base segments 50 is arranged along an outwardly convex path in a transverse plane relative to an axis defined by the support structure 32. The base edge 41 of the flexible leaflets 43 has a path corresponding to the path of the groups 62 of base segments 50. As will be described in more detail below, a string 26 extends through the base portion 52 of each post 38 and all of the base segments 50.

Each base segment 50, and the base portion 52 of each post 38, has a male engagement surface 54a at a first end or side and a female engaging surface 54b at a second end or side opposite the first end or side. Each male engagement surface 54a is configured for engagement with a complementary female engagement surface 54b of an adjacent base segment 50 or an adjacent base portion 52 of a post 38.

Each of the base segments 50 has a tunnel 56 extending through it (see FIG. 6B) between the engagement surfaces 54a, 54b of the base segment 50. The base portion 52 of each post 38 has two tunnels 58a, 58b extending through it. Each base portion tunnel 58a, 58b has a first end at respective engagement surfaces 54 on opposite sides of the post 38. Each base portion tunnel 58a, 58b has a second end at a radially outer surface 60 of the post 38. The string 26 (see FIG. 6B) extends through the base segment tunnels 56 and the base portion tunnels 58a, 58b and forms loops 26a, 26b, 26c between the base portion tunnel 58a and the base portion tunnel 58b at each post 38.

The artificial heart valve 24 is expanded by applying tension to the loops 26a, 26b, 26c until adjacent engagement surfaces 54 are pulled into engagement so that the base segments 50 and the base portion 52 of each post 38 are engaged and the posts 38 are aligned side-by-side and evenly distributed around the annular base 36 as shown in FIG. 6A. When the artificial heart valve is in the expanded operational configuration the support structure is rigid.

As tension in the string 26 pulls the engagement surfaces 54 of the base segments 50 and the base portion 52 of each post 38 into engagement, the base 36 of the support structure 32 forms within the channel formed by the flexible leaflets 34 such that the flexible leaflets 34 cover the radially outer surface 64 of each base segment 50.

When the artificial heart valve 24 is in the collapsed delivery configuration (see FIG. 6B), the posts 38 are located side-by-side and spaced closer together for mounting on the catheter 16. The flexible leaflets 34 fold up between the posts 38. Each flexible leaflet 34 folds in a predictable manner consistent with the approximate "S" shape of the free edge 42 of the flexible leaflet 34. To allow the posts 38 to be positioned closer together, the engagement surfaces 54 of the base segments 50 and the base portion 52 of each post 38 are disengaged and spaced apart so that each group 62 of base segments 50 hangs on the string 26 between two adjacent posts 38.

Each post 38 has a string guidance feature in the form of a ring protruding from the post. The ring 66 is located on the radially outer surface 60 of the post 38. Where the post 38 has a length measured between the bottom of the post 38 and the top of the post 38, the ring 66 is located approximately three quarters of the length from the bottom of the post 38.

Figure 7:
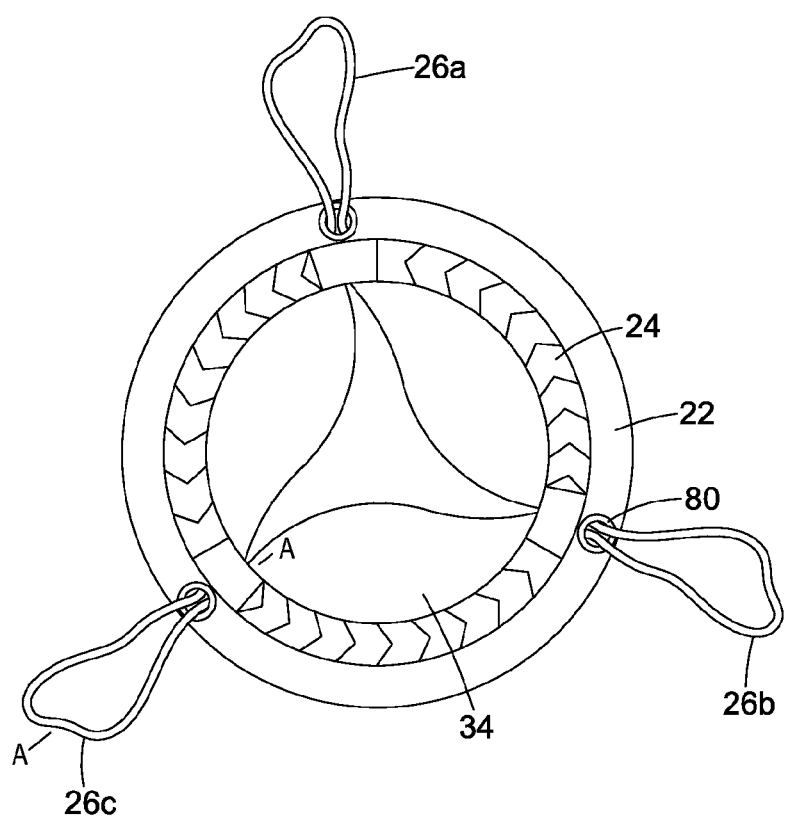
FIG. 7 is a plan view of the artificial heart valve system of FIG. 1.

As can be seen in FIG. 7, in the expanded operational configuration, the artificial heart valve 24 is circumferentially engaged with the stent 22.

Figure 8C:
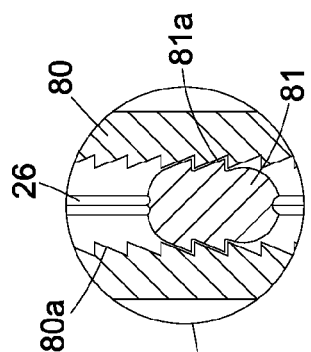
FIG. 8C is a detailed view of the locking arrangement of FIGS. 8A and 8B.
Figure 8B:
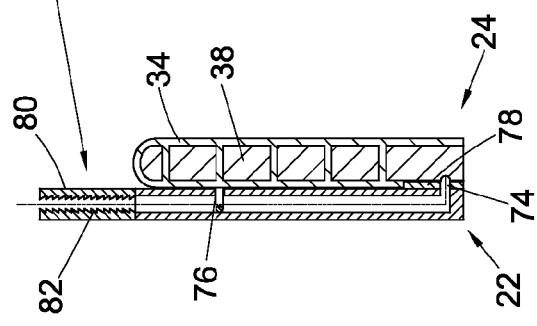
FIG. 8B is a section on line A-A of FIG. 7, after expansion of the artificial heart valve system.
Figure 8A:
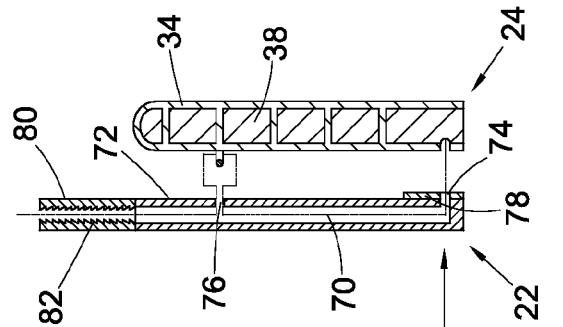
FIG. 8A is a section on line A-A of FIG. 7, during expansion of the artificial heart valve system.

Referring to FIGS. 8A and 8B, the stent 22 defines a plurality of string guidance features. Each string guidance feature may comprise a channel 70. At least one channel 70 is associated with each post 38 of the artificial heart valve 24. The string guidance features may further comprise apertures extending through the stent 22 from the radially inner surface 72 of the stent 22 to the channel 70. A bottom aperture 74 is associated with the base portion tunnels 58a, 58b. The channel 70 extends from the top of the stent 22 to the bottom aperture 74. The top aperture 76 is associated with the ring 66 of the post 38. Where the stent 22 has a length measured between the top of the stent 22 and the bottom of the stent, the top aperture 76 is located approximately three quarters of the length from the bottom of the stent 22. A bottom portion of the channel 70 extends between the bottom aperture 74 and the top aperture 76. A top portion of the channel 70 extends between the top aperture 76 and the top of the stent 22.

The path of a loop 26a, 26b, 26c of the string 26 is shown in FIGS. 8A and 8B as a dashed string. As will be described in more detail below, the string 26 extends through the string guidance features alternatingly between the support structure 32 and the stent 22. Specifically, a loop 26a, 26b, 26c of the string 26 extends from the second end of the base portion tunnels 58a, 58b, through the bottom aperture 74, through the bottom portion of the channel 70, through the top aperture 76, through the ring 66, returns through the top aperture 76, and extends through the top portion of the channel 70 and out of the stent 22. When tension is applied to the loops 26a, 26b, 26c, the artificial heart valve 24 is simultaneously moved from the collapsed configuration to the expanded configuration, and brought into axial alignment and circumferential engagement with the stent 22. FIGS. 7 and 8B show the artificial heart valve 24 in engagement with the stent 22. The portion of the flexible leaflets 34 that covers the base 36 of the support structure 32 is compressed between the artificial heart valve 24 and the stent 22.

Figure 8D:
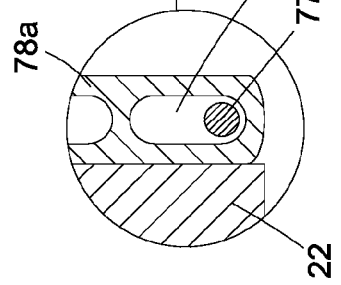
FIG. 8D is a detailed view of a sealing arrangement of FIGS. 8A and 8B.

As shown in FIGS. 8A and 8B, a sealing arrangement 78 is provided between the flexible leaflets 34 of artificial heart valve 24 and the stent 22 adjacent the base 36 of the support structure 32. As shown in more detail in FIG. 8D, the sealing arrangement 78 includes a sealing member 78a which has an annular channel 79. The sealing arrangement 78 further includes a sealing actuation string 77 which passes through the annular channel 79. Both ends of the sealing actuation string 77 pass through a point on a radially inner surface of the annular sealing member 78 such that tension can be applied to the sealing actuation string 77. On application of tension to the sealing actuation string 77, the sealing actuation string 77 compresses a portion of the annular sealing member 78a and a radially outer portion of each flexible leaflet 34 against the radially outer surface of the support structure 32 so as to form a circumferentially continuous seal between the stent 22 and the artificial heart valve 24 which serves to reduce or prevent leakage of blood between the stent 22 and the artificial heart valve 24.

A plurality of string locking arrangements is provided. Each string locking arrangement may include a female locking element in the form of a cylindrical locking tube 80 located above each channel 70 in the stent 22. Each locking tube 80 is a hollow cylinder. The radially inner surface 80a of the locking tube 80 is ridged. On exit from the stent channel 70, the loop 26a, 26b, 26c extends through the locking tube 80. Each string locking arrangement may include a male locking element in the form of a polymer bead 81 (see FIG. 8C) provided on the string 26. The radially outer surface 81a of the polymer bead 81 is ridged. The polymer bead 81 enters the locking tube 80 such that the ridged surfaces 80a and 81a of the locking tube 80 and the polymer bead 81 engage one another when the artificial heart valve has been fully expanded. The engagement between the ridged surfaces 80a, 81a acts to prevent the loop 26a, 26b, 26c of the string 26 from moving back through the locking tube 80 towards the stent 22. Tension in the loops 26a, 26b, 26c is maintained and the artificial heart valve 24 is locked in the expanded configuration in engagement with the stent 22.

The process of percutaneously implanting the artificial heart valve system 10 into the aorta 12 of the heart 14 will now be described with reference to FIGS. 9A, 9B, 9C and 10.

Figure 9A:
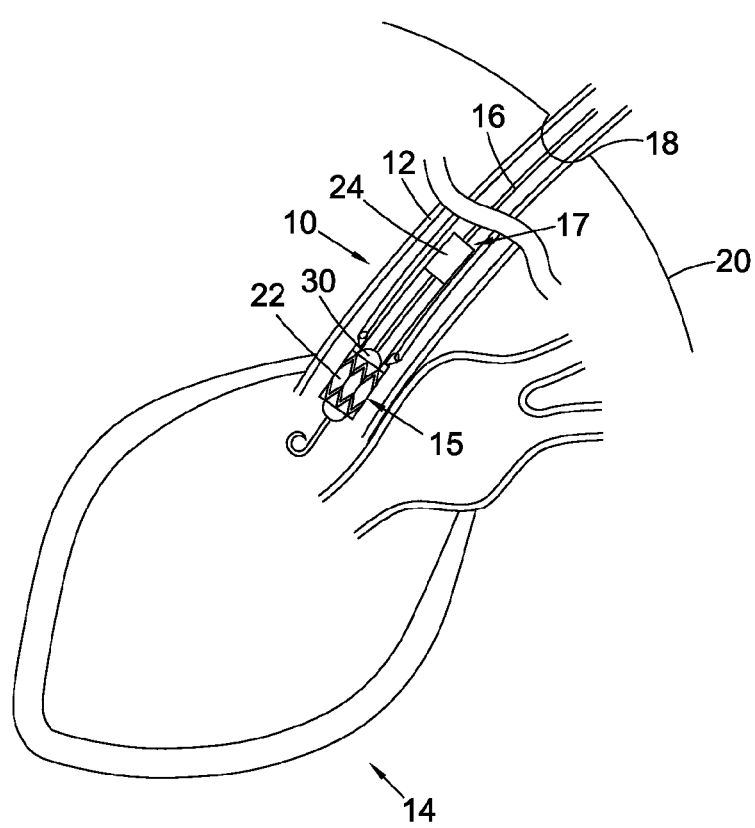
FIG. 9A is a schematic cross-section during percutaneous delivery of an artificial heart valve system to the aorta before expansion of a stent.

With reference to FIG. 9A, the artificial heart valve system 10 is mounted on a catheter 16 with the stent 22 and artificial heart valve 24 in their respective collapsed delivery configurations. The stent 22 and an inflatable member 30 are mounted on the catheter 16 at a first axial location 15 with the stent 22 located radially outwardly of the inflatable member 30. The artificial heart valve 24 is mounted on the catheter 16 at a second axial location 17. The second axial location 17 on the catheter 16 is proximal relative to the first axial location 15 on the catheter 16, i.e. closer to the incision 18 in the skin 20. The catheter 16 is inserted through an incision 18 in the skin 20 of the subject and through an artery to the aorta 12.

Figure 9B:
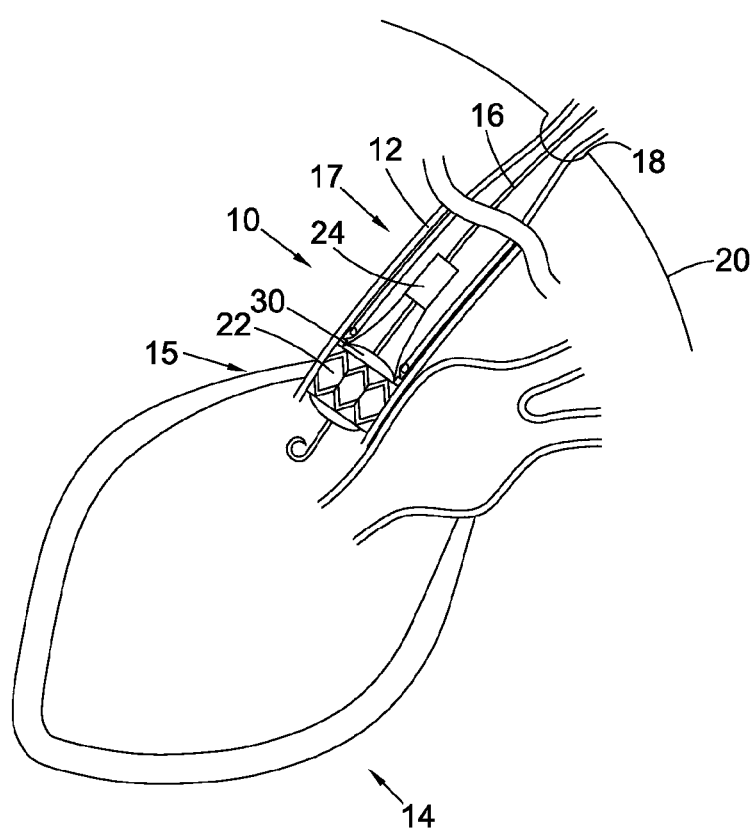
FIG. 9B is a schematic cross-section during percutaneous delivery of an artificial heart valve system, after expansion of the stent but before expansion of a heart valve.

Referring to FIG. 9B, the inflatable member 30 is inflated to expand the stent 22 within the aorta 12 from its collapsed delivery configuration to its expanded operational configuration.

Figure 9C:
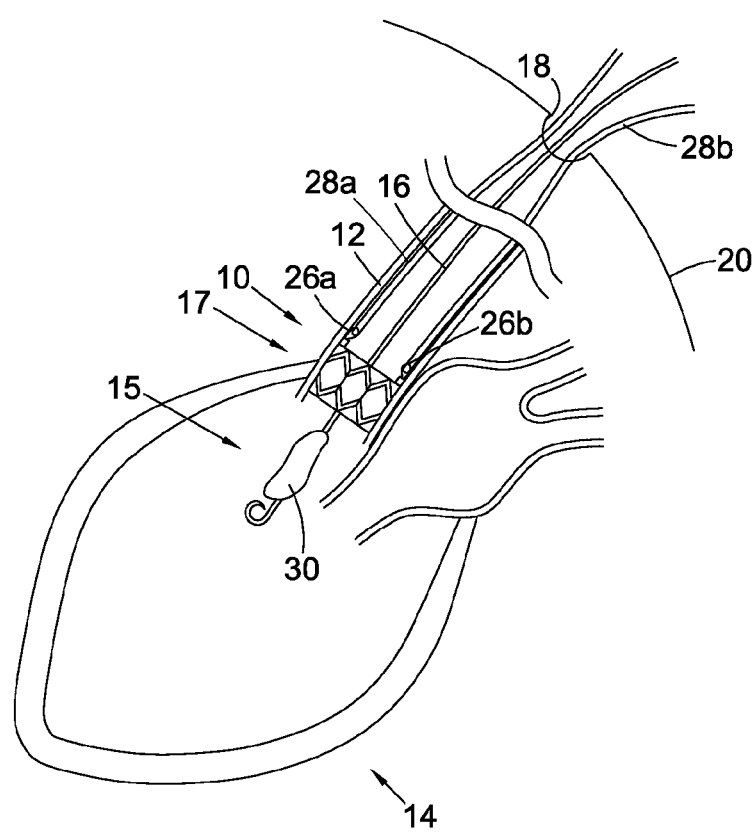
FIG. 9C is a schematic cross-section during percutaneous delivery of an artificial heart valve system, after expansion of the stent and the heart valve, but before removal of secondary strings.
Figure 10:
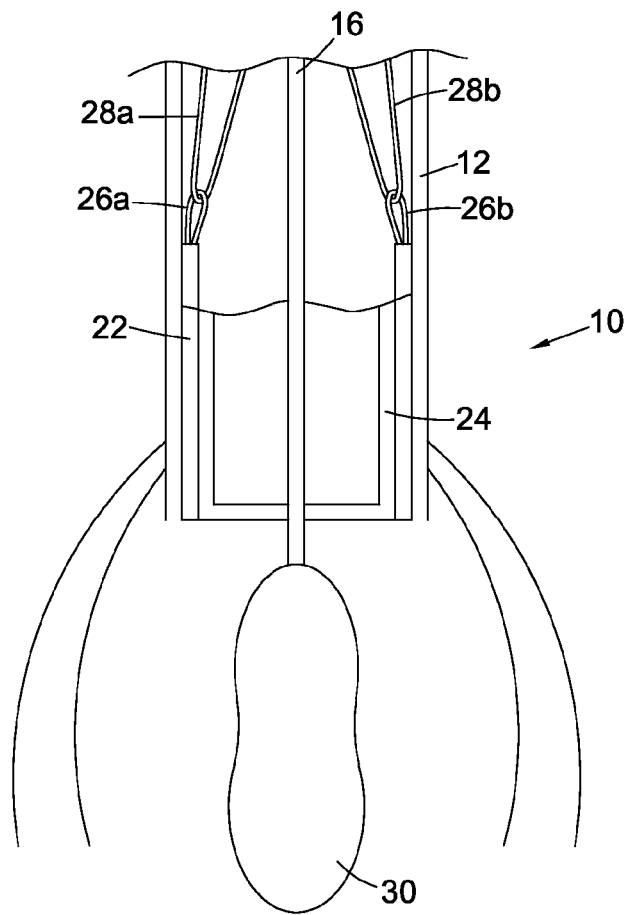
FIG. 10 is a detailed schematic cross-section during percutaneous delivery of an artificial heart valve system corresponding to FIG. 9C.

Referring to FIGS. 9C and 10, once the stent 22 is expanded, the inflatable member 30 is deflated. As one of ordinary skill in the art will understand, the stent 22 is configured such that, once expanded, the stent 22 remains in an expanded operational configuration. The catheter 16 is inserted into the subject further until the artificial heart valve 24 is generally aligned axially with the stent 22. One of ordinary skill in the art will understand that a sleeve (not shown) may cover the artificial heart valve 24 whilst it is mounted on the catheter 16 for delivery. The sleeve (not shown) is removed using a secondary string (not shown) connected to the sleeve (not shown) and extending to the incision 18. The artificial heart valve 24 is then expanded and pulled radially outwardly into engagement with the stent 22. Specifically, the artificial heart valve 24 is expanded by applying tension to secondary strings 28a, 28b, 28c. Each secondary string 28a, 28b, 28c extends from an incision 18 in the skin 20 of the subject, through a corresponding loop 26a, 26b, 26c, of the string 26 and returns to the incision 18. The tension applied to the secondary strings is translated to the loops 26a, 26b, 26c of the string 26. As described above, on application of tension to the loops 26a, 26b, 26c, the artificial heart valve 24 moves from the collapsed delivery configuration to the expanded operational configuration.

One skilled in the art will understand that various modifications may be made to the foregoing embodiments without departing from the scope of the present invention as defined by the appended claims.

Figure 11A:
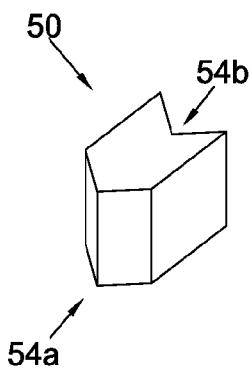
FIG. 11A is a perspective view of a base segment of FIG. 6.
Figure 11B:
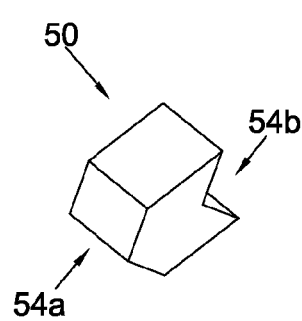
FIG. 11B is a perspective view of an alternative base segment.
Figure 11C:
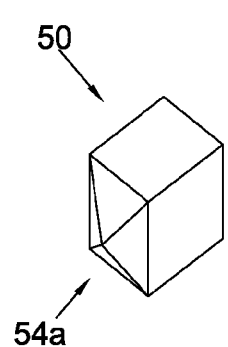
FIG. 11C is a perspective view of a further alternative base segment.

For example, each of FIGS. 11A, 11B and 11C, shows an alternative support element in the form of an alternative base segment 50. Each alternative base segment defines a male engagement surface 54a at a first end or side and a female engagement surface 54b at a second end or side opposite the first end or side. In a first alternative base segment shown in FIG. 11A, each of the engagement surfaces 54a, 54b is defined by two planar surfaces which meet along an edge which is aligned generally parallel to an axis of the artificial heart valve when the artificial heart valve is in the expanded operational configuration and the engagement surfaces 54a, 54b are inter-engaged such that the engagement surfaces 54a, 54b prevent relative radial movement between adjacent base segments 50. One of skill in the art will also understand that each post 38 may define male and female engagement surfaces like the male and female engagement surfaces 54a, 54b of the first alternative base segments shown in FIG. 11A so that when the artificial heart valve is in the expanded operational configuration and the engagement surfaces are inter-engaged, the engagement surfaces prevent relative radial movement between a post 38 and an adjacent base segment 50.

In a second alternative base segment shown in FIG. 11B, each of the engagement surfaces 54a, 54b is defined by two planar surfaces which meet along an edge which is aligned generally perpendicular to an axis of the artificial heart valve when the artificial heart valve is in the expanded operational configuration and the engagement surfaces 54a, 54b are inter-engaged such that the engagement surfaces 54a, 54b prevent relative axial movement between adjacent base segments. One of skill in the art will also understand that each post 38 may define male and female engagement surfaces like the male and female engagement surfaces 54a, 54b of the second alternative base segments shown in FIG. 11B so that when the artificial heart valve is in the expanded operational configuration and the engagement surfaces are inter-engaged, the engagement surfaces prevent relative axial movement between a post 38 and an adjacent base segment 50.

In a third alternative base segment shown in FIG. 11C, each of the engagement surfaces 54a, 54b is defined by four planar surfaces which meet along four edges when the artificial heart valve is in the expanded operational configuration and the engagement surfaces 54a, 54b are inter-engaged such that the engagement surfaces 54a, 54b prevent relative radial and relative axial movement between adjacent base segments. One of skill in the art will also understand that each post 38 may define male and female engagement surfaces like the male and female engagement surfaces 54a, 54b of the third alternative base segments shown in FIG. 11C so that when the artificial heart valve is in the expanded operational configuration and the engagement surfaces are inter-engaged, the engagement surfaces prevent relative radial and relative axial movement between a post 38 and an adjacent base segment 50.

In each of the alternative base segments shown in FIGS. 11A-11C, the angle at which the planar surfaces meet may be between approximately 60 degrees and approximately 120 degrees. The planar surfaces may meet an angle of 90 degrees. Alternatively, the planar surfaces may meet at an angle of 120 degrees.

Figure 12A:
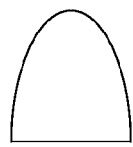
FIG. 12A is a cross-section of a first alternative base segment.
Figure 12B:
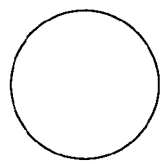
FIG. 12B is a cross-section of a second alternative base segment.
Figure 12C:
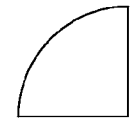
FIG. 12C is a cross-section of a third alternative base segment.

The base segments 50 may have a cross-sectional profile other than the rectangular cross-sectional profile shown in FIGS. 5A and 5B. For example, each base segment 50 may have a rounded upper surface as shown in FIG. 12A. In other embodiments, the base segments may have a circular cross-section as shown in FIG. 12B. In yet other embodiments, the base segments may have a cross-section comprising a square or rectangle with a rounded corner as shown in FIG. 12C. The rounded corner is the radially outer top corner of the base segment. Compared with the radially outer top corner of the base segments shown in shown in FIGS. 5A and 5B, the rounded corner may serve to reduce localized pressure on the flexible leaflets 34 at the rounded corner. The rounded corner may be shaped so as to be commensurate with the shape of the flexible leaflets 34. It should be understood that the base segments 50 may have one of the cross-sectional profiles shown in any of FIGS. 12A-12C in combination with one pair of male and female engagement surfaces 54a, 54b shown in any of FIGS. 11A-11C. Alternatively, the base segments 50 may have one of the cross-sectional profiles shown in any of FIGS. 12A-12C in combination with a conical male engagement surface (not shown) and a conical female engagement surface (not shown).

Figure 13:
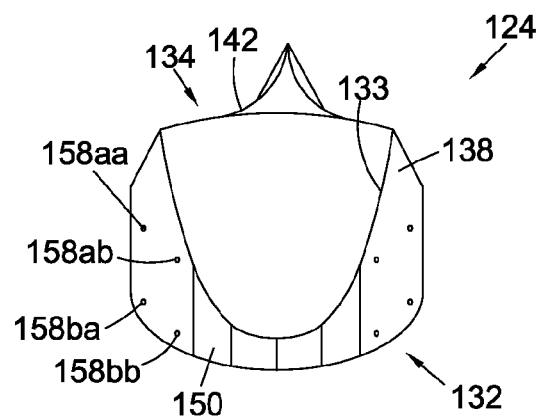
FIG. 13 is a perspective view of an alternative artificial heart valve which is suitable to be delivered percutaneously.

An alternative embodiment of an artificial heart valve is shown in FIG. 13. Features of this embodiment that correspond to those of the previously described embodiment use corresponding reference numerals incremented by "100". The artificial heart valve 124 has a plurality of support elements and flexible leaflets 134. When the artificial heart valve 124 is in the expanded operational configuration, the plurality of support elements forms a generally cylindrical support structure 132. An upper edge 133 of the support structure 132 defines a plurality of generally U-shaped or "scalloped" regions. The flexible leaflets 134 extend across the scalloped regions. A base edge of each flexible leaflet 134 has a generally U-shaped or "scalloped" shape defined by the corresponding U-shaped or "scalloped" region of the upper edge 133 of the support structure 132. Each leaflet 134 has a movable free edge 142 located opposite the corresponding U-shaped or "scalloped" region of the upper edge 133 of the support structure 132. The support structure 132 is segmented circumferentially into a plurality of base segments 150 and a plurality of posts 138. Each flexible leaflet 134 is attached to two of the posts 138. Each base segment 150 has upper and lower tunnels (not shown) for receipt of first and second strings (not shown). Each post 138 has two upper tunnels 158aa, 158ab and two lower tunnels 158ba, 158bb for receipt of first and second strings (not shown). The first string (not shown) forms a loop between the two upper tunnels 158aa, 158ab of each post 138. The second string (not shown) forms a loop between the two lower tunnels 158ba, 158bb of each post 138. In use, the loops formed in the first and second strings extend through a stent (not shown). Tension on the loops formed in the first and second strings (not shown) pulls the artificial heart valve 124 from a collapsed delivery configuration to an expanded operational configuration whilst also pulling the artificial heart valve 124 into engagement with the stent (not shown).

Figure 14:
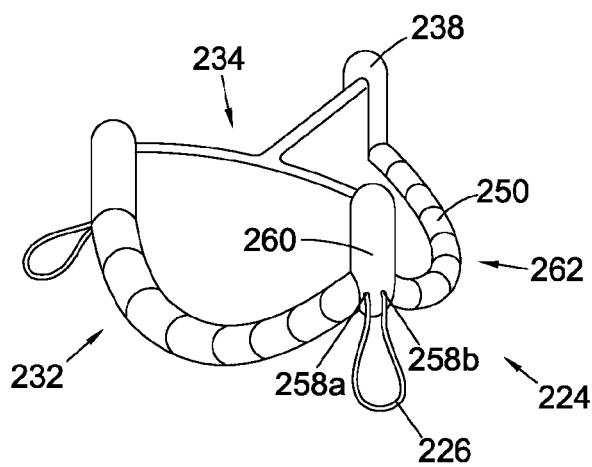
FIG. 14 is a perspective view of a further alternative artificial heart valve which is suitable to be delivered percutaneously.

A further alternative embodiment of an artificial heart valve is shown in FIG. 14. Features of this embodiment that correspond to those of the first described embodiment use corresponding reference numerals incremented by "200". The artificial heart valve 224 has a plurality of support elements and flexible leaflets 234. When the artificial heart valve is in the expanded operational configuration the support elements together form a support structure 232 defining an aperture for blood flow. The plurality of support elements includes three posts 238 and a plurality of base segments 250. Between each pair of adjacent posts 238 there is a group 262 of base segments. A string 226 extends through the posts 238 and the base segments 250. When the artificial heart valve 224 is in the expanded operational configuration, each group 262 of base segments 250 is arranged along an outwardly convex path having both circumferential and axial components relative to an axis defined by the aperture for blood flow. Each of the base segments 250 has a tunnel (not shown) for receipt of a string. Each post 238 has two tunnels 258*a* and 258*b*. Each tunnel 258*a* and 258*b* extends from an adjacent base segment 250 to a radially outer surface 260 of the post 238. Loops are formed in the string 226 between the tunnels 258*a* and 258*b*.

One skilled in the art will understand that other modifications may be made to the foregoing embodiments without departing from the scope of the present invention as defined by the appended claims. For example, each flexible leaflet may be attached, for example, fused, bonded or sewn to at least one base segment. For example, each flexible leaflet may be attached to a base segment in the middle of the group of base segments to which said base segment belongs. Attaching each flexible leaflet to at least one base segment may assist in guiding the base segments into the channel defined along the base edge of the flexible leaflet when the artificial heart valve is expanded from the collapsed delivery configuration to the expanded operational configuration. Furthermore, by having at least one base segment per group attached to the flexible leaflet, a distance by which the base segments extend below the base edges of the flexible leaflets when the artificial heart valve is in the collapsed delivery configuration is reduced in comparison to a distance by which the base segments extend below the base edges of the flexible leaflets when none of the base segments are fixed to the flexible leaflet. This may reduce the chance of damage to the artificial heart valve in the event of heart ejection during delivery of the artificial heart valve.

An artificial heart valve may be delivered such that it replaces the aortic valve, the mitral valve or any other valve within the heart. An artificial heart valve may comprise fewer or more than three posts and fewer or more than three flexible leaflets, provided that the number of leaflets corresponds to the number of posts. Similarly, the number of string guidance features in the stent may vary to correspond to the number of posts.

The flexible leaflets may be manufactured using any suitable method such as injection molding, dip molding or the like. A leaflet material may be formed around and/or through the posts so as to define the flexible leaflets. The leaflet material may extend continuously around and/or through the posts. Each post may define one or more apertures or slits through which the leaflet material extends. The leaflet material may be formed around and/or through one or more of the base segments so as to define the flexible leaflets. The leaflet material may extend continuously around and/or through one or more of the base segments. Each base segment may define one or more apertures or slits through which the leaflet material extends.

The flexible leaflets may comprise or be made of any suitable material, provided that the flexible leaflets can fold sufficiently to allow the artificial heart valve to assume the collapsed delivery configuration. For example, the flexible leaflets may comprise or be formed of a natural material such as human aortic or pulmonary valves, animal aortic or venous valves, or animal pericardium. The flexible leaflets may comprise or be formed of a synthetic polymer such as polyurethane.

The support elements may comprise, or be formed of, any suitable material. For example, the support elements may comprise, or be formed from, a metal. The support elements may comprise, or be formed of, stainless steel, titanium, or a polymer such as polyether ether ketone (PEEK). The support elements may have a rough or textured surface. A rough or textured surface may improve the adhesion of the leaflet material to the support elements. The support elements may comprise, or be formed of, a sintered material. Use of a sintered material may provide the support elements with a rough or textured surface. The support elements may be formed using an additive manufacturing technique. For example, the support elements may be formed by direct laser sintering such as direct laser metal sintering and/or by 3-D printing.

There may be more tunnels, strings and loops than described above. One, two or more tunnels may be provided in each base segment, wherein each tunnel receives a corresponding string. The tunnels may be substantially parallel, or may have dissimilar paths. The tunnels may be curved or straight. A string may be provided per group of base segments. A loop may be formed at each end of each string.

One or more of the strings may comprise or be formed from a cord, a line, a ligature, a suture, a thread or the like. One or more of the strings may be coated in polymer. The polymer may be configured so as to provide an interference fit between the string and the tunnel of each support element through which the string passes. Such an interference fit may be selected so that the string is not loosely fitted in the tunnel. Such an interference fit may be selected so that each support element through which the string passes does not slide along the string unless a predetermined force is applied between the support element and the string. This may prevent the support element from moving along the string without user manipulation. The polymer may comprise polyester, such as braided polyester.

The number of base segments per group of the base may be fewer or more than ten depending on the size of the artificial heart valve, the size of the base segments, the number of posts, etc. The engagement surfaces can have any suitable form such that each engagement surface abuts or inter-engages a complementary adjacent surface, whether of a base segment or a base portion of a post.

Although the string guidance feature of the post is described above as a ring or eyelet protruding from the post, the string guidance feature may be constructed in any other suitable manner such that the loop can pass through the string guidance feature. For example, the string guidance feature may be a generally "U" shaped tunnel on the radially outer face of the post. The location of the string guidance feature and the corresponding stent aperture can be closer to the top or closer to the bottom of the artificial heart valve system than the three quarter distance described previously, provided that the artificial heart valve can be suitably engaged with the stent on application of tension to the loops.

Separate strings may be provided to extend between the tunnels in the support elements and the stent, and between the post string guidance feature and the stent. For example, the previously described one or more strings may extend between the tunnels in the support elements and the stent, and one or more anchor strings may extend between the post string guidance features and the stent. The one or more anchor strings may not extend through any of the base segments. The system may comprise one or more secondary strings for applying tension to the one or more anchor strings.

The locking tubes may be integrally formed with the stent. The locking tubes may be located within the stent.

In the method of percutaneously implanting the artificial heart valve 24 described with reference to FIGS. 9A to 9C and 10, the stent 22 and the inflatable member 30 are mounted on the catheter 16 at a first axial location of the catheter 16 with the stent 22 located radially outwardly of the inflatable member 30 and the artificial heart valve 24 is mounted on the catheter at a second axial location on the catheter 16, where the second axial location of the artificial heart valve 24 on the catheter 16 is proximal with respect to the first axial location of the stent 22 and the inflatable member 30. Initially, the catheter 16 is inserted into the subject until the stent 22 and the inflatable member 30 are generally aligned axially with the valve annulus. The inflatable member 30 is inflated to expand the stent 22 from its collapsed delivery configuration to its expanded operational configuration. The inflatable member 30 is deflated after expansion of the stent 22. The catheter 16 is inserted further into the subject until the artificial heart valve 24 is generally aligned axially with the stent 22 and the inflatable member 30 is inserted distally of the stent 22. Once the artificial heart valve 24 is expanded, the inflatable member 30 is retracted back through the expanded artificial heart valve 24. In effect, therefore, mounting the artificial heart valve 24 on the catheter 16 at a second axial location which is proximal with respect to the first axial location of the stent 22 and the inflatable member 30, may avoid any requirement for the artificial heart valve 24 to be inserted into, or through, the valve annulus before expansion of the stent 22.

Alternatively, the artificial heart valve may be mounted on the catheter at a second axial location which is distal with respect to the first axial location of the stent and the inflatable member. The method may then comprise inserting the catheter into the subject so as to insert the artificial heart valve through the valve annulus until the stent and the inflatable member are generally aligned axially with the valve annulus. The method may comprise inflating the inflatable member to expand the stent from its collapsed delivery configuration to its expanded operational configuration. The method may comprise deflating the inflatable member after expansion of the stent. The method may comprise retracting the catheter from the subject until the artificial heart valve is generally aligned axially with the stent for expansion of the artificial heart valve and the inflatable member is proximal of the stent.

The invention claimed is:

1. An artificial heart valve suitable to be delivered percutaneously, comprising:
    a plurality of support elements in the form of a plurality of base segments and a plurality of posts;
    a plurality of flexible leaflets, each leaflet attached to two of the posts; and
    one or more strings passing through the plurality of support elements,
    wherein the artificial heart valve is configurable between a collapsed delivery configuration in which the posts are located side-by-side and closer together and an expanded operational configuration in which the posts are located side-by-side and further apart, and
    wherein, when the artificial heart valve is in the collapsed delivery configuration, application of tension to the one or more strings pulls each support element into engagement with adjacent support elements until the artificial heart valve adopts the expanded operational configuration in which the support elements together form a support structure defining an aperture for blood flow and in which the leaflets are movable between an open configuration in which the leaflets permit blood flow through the artificial heart valve and a closed configuration in which the leaflets restrict blood flow through the artificial heart valve.

2. The artificial heart valve according to claim 1, wherein, when the artificial heart valve is in the expanded operational configuration, the support elements are in compression, and when the artificial heart valve is in the collapsed delivery configuration the support elements are not in compression.

3. The artificial heart valve according to claim 1, wherein the support structure is generally annular or generally cylindrical and, optionally, wherein the posts are distributed circumferentially around the support structure with an equal number of base segments located between adjacent posts and, optionally, wherein the artificial heart valve comprises the plurality of base segments, typically 10 to 16 base segments, between each pair of adjacent posts.

4. The artificial heart valve according to claim 1, wherein adjacent support elements define complementary surfaces which are in engagement when the artificial heart valve is in the expanded operational configuration.

5. The artificial heart valve according to claim 1, wherein each post has a base portion and, optionally, wherein, for each post, the base portion of the post and the base segment adjacent to the base portion of the post define complementary surfaces which are in engagement when the artificial heart valve is in the expanded operational configuration.

6. The artificial heart valve according to claim 1, wherein, when the artificial heart valve is in the expanded operational configuration, each leaflet extends over one or more of the base segments between the two posts to which the leaflet is attached, wherein each leaflet defines a base edge, the base edge defines a channel or recess, the channel or recess has an internal profile, the one or more base segments between the two posts to which the leaflet is attached define an external profile, and wherein the internal profile of the channel or recess is complementary to the external profile defined by the one or more base segments between the two posts to which the leaflet is attached.

7. The artificial heart valve according to claim 1, wherein each flexible leaflet comprises a polymer and/or wherein each support element comprises a metal.

8. The artificial heart valve according to claim 1, wherein each flexible leaflet is bonded or fused to at least one base segment located between the posts to which the flexible leaflet is attached.

9. The artificial heart valve according to claim 1, wherein, when the artificial heart valve is in the expanded operational configuration, the base segments between each pair of adjacent posts are arranged along an outwardly convex path in a transverse plane relative to an axis defined by the aperture for blood flow and, optionally, wherein each leaflet has a moveable free edge and a base edge opposite the free edge and, wherein, when the artificial heart valve is in the expanded operational configuration, the moveable free edge is generally S-shaped and the base edge is outwardly convex relative to the axis defined by the aperture for blood flow.

10. The artificial heart valve according to claim 1, wherein, when the artificial heart valve is in the expanded operational configuration, the base segments between each pair of adjacent posts are arranged along an outwardly convex path having both circumferential and axial components relative to an axis defined by the aperture for blood flow and, optionally, wherein each leaflet has a moveable free edge and a base edge opposite the free edge and, wherein, when the artificial heart valve is in the expanded operational configuration, the base edge is arranged along the outwardly convex path having both circumferential and axial components relative to the axis defined by the aperture for blood flow.

11. An artificial heart valve system suitable to be delivered percutaneously, the artificial heart valve system comprising:
the artificial heart valve according to claim 1; and
a stent configurable between a collapsed delivery configuration and an expanded operational configuration;
wherein the one or more strings pass through the stent, and
wherein, when the stent is in its expanded operational configuration and the artificial heart valve is in its collapsed delivery configuration, application of tension to the one or more strings pulls each support element into engagement with adjacent support elements and pulls the posts into engagement with the stent until the artificial heart valve adopts the expanded operational configuration and is in engagement with the stent.

12. The artificial heart valve system according to claim 11, wherein the one or more strings pass alternatingly through the stent and the plurality of support elements of the artificial heart valve.

13. The artificial heart valve system according to claim 11, wherein the stent comprises at least one string guidance feature corresponding to each post, and wherein the one or more strings extend through the string guidance features and, optionally, wherein, when the stent is in its expanded operational configuration and the artificial heart valve is in its expanded operational configuration, each post abuts the stent at a location adjacent the corresponding at least one string guidance feature and, optionally, wherein each post comprises a plurality of tunnels through which the one or more strings pass, and each base segment comprises a tunnel through which the one or more strings pass and, optionally, wherein, for each post, the one or more strings pass from at least one of the tunnels of the post through a corresponding string guidance feature of the stent and, optionally, wherein each post comprises the string guidance feature and, optionally, wherein, for each post, the one or more strings pass from at least one of the tunnels of the post through a first corresponding string guidance feature of the stent, through the corresponding string guidance feature of the post, and through a second corresponding string guidance feature of the stent.

14. The artificial heart valve system according claim 11, wherein the one or more strings comprise a single continuous string.

15. The artificial heart valve system according to claim 11, wherein the one or more strings comprise a plurality of strings, and wherein, for each pair of adjacent posts, one of the strings extends through each base segment located between the pair of adjacent posts, through the pair of adjacent posts, and through the stent.

16. The artificial heart valve system according to claim 11, wherein the one or more strings comprise a plurality of strings, and, for each pair of adjacent posts, two or more of the strings extend through each base segment located between the pair of adjacent posts, through the pair of adjacent posts, and through the stent.

17. The artificial heart valve system according claim 11, wherein, when the stent is in its expanded operational configuration and the artificial heart valve is in its expanded operational configuration, the support structure abuts a surface of the stent which is radially inward relative to an axis defined by the aperture for blood flow.

18. The artificial heart valve system according to claim 11, comprising a plurality of string locking arrangements, wherein each string locking arrangement is configured to allow the one or more strings to be pulled in a first direction relative to the stent but to prevent the one or more strings from being pulled relative to the stent in a second direction opposite to the first direction.

19. The artificial heart valve system according to claim 11, comprising a sealing arrangement configured to provide a seal between the artificial heart valve and the stent when the stent is in its expanded operational configuration and the artificial heart valve is in its expanded operational configuration and, optionally, wherein the sealing arrangement extends around a base portion of the stent and, optionally, wherein the sealing arrangement comprises a sealing member and a flexible sealing actuation string extending around a periphery of the sealing member, and wherein, when the stent is in its expanded operational configuration and the artificial heart valve is in its expanded operational configuration, tension applied to the sealing actuation string compresses the sealing member and the plurality of flexible leaflets against the support structure.

* * * * *